US006589220B2

(12) United States Patent
Taylor

(10) Patent No.: US 6,589,220 B2
(45) Date of Patent: Jul. 8, 2003

(54) DISPOSABLE CONTAINER FOR EMESIS

(76) Inventor: Joyce Mae Taylor, 6692 Cheryl Ann Dr., Independence, OH (US) 44131-3719

(*) Notice: Subject to any disclaimer, the term of this patent is extended or adjusted under 35 U.S.C. 154(b) by 0 days.

(21) Appl. No.: 09/901,877

(22) Filed: Jul. 9, 2001

(65) Prior Publication Data

US 2003/0009140 A1 Jan. 9, 2003

(51) Int. Cl.[7] .................................................. A61M 1/00
(52) U.S. Cl. ...................................................... 604/323
(58) Field of Search ................................. 604/322–323, 604/317, 319, 327, 355, 356; 4/258; D11/143; 248/102, 96, 163.1

(56) References Cited

U.S. PATENT DOCUMENTS 317,251 A * 5/1885 Walton .......................... 4/258
1,023,669 A * 4/1912 Megill ........................... 4/258
3,797,734 A * 3/1974 Fleury et al. ................. 383/36
3,920,179 A * 11/1975 Hall .................... 128/DIG. 24
4,990,145 A * 2/1991 Fleury ........................ 604/317
5,067,821 A * 11/1991 Young .......................... 383/36
5,599,332 A 2/1997 Cashel
5,871,183 A * 2/1999 Milluzzi ..................... 224/274
5,957,038 A * 9/1999 Shimazaki ................... 99/340

* cited by examiner

*Primary Examiner*—Weilun Lo
*Assistant Examiner*—C. Lynne Anderson
(74) *Attorney, Agent, or Firm*—Forrest L. Collins

(57) ABSTRACT

A container for receiving and containing emesis is provided. The container is compact, easily transported, and disposable. The container includes a hollow body member having an open neck and a closed base, a mouthpiece for receiving and directing the flow of emesis into the body member, and a local restriction to prevent spillage or splash back. The containers are collapsible along a central axis for compact storage. An emesis collection system utilizes the collection container, a storage box for holding a plurality of containers, and a holder.

21 Claims, 4 Drawing Sheets

DISPOSABLE CONTAINER FOR EMESIS

BACKGROUND OF THE INVENTION

1. Field of Invention

This invention pertains to the field of health care, and more specifically, to a container for receiving and containing emesis.

2. Description of the Related Art

The present invention contemplates a new and improved container for receiving and containing emesis, which is simple in design, effective in use, and overcomes the foregoing difficulties and others, while providing better and more advantageous over-all results.

Typically, hospitals, doctors' facilities and small clinics and the like use basins, which are open, shallow, kidney-shaped, plastic pans for the collection of emetic or like matter. Unfortunately, these basins are large and bulky which makes it difficult to store them in an easily accessible place for patients. Further, the open top of the basins often results in undesirable splashing and spillage of the emesis.

Similarly, during times of nausea occurring in the home or other common areas, trash cans, paper/plastic bags, towels or any available receptacle is used to receive emetic or like matter. Unfortunately, the use of these devices often result in spills onto clothing, carpets, floors, furniture, car interiors, walls, etc.

U.S. Pat. No. 5,599,332 purports to provide a portable receptacle for receiving emesis. The receptacle having a fairly complicated design. Such a design would hinder making the product disposable. Further, the receptacle is bulky and not readily stored in a compact manner.

A need remains in the art for a receptacle for receiving emesis and the like which is simple in design, convenient to store, and disposable, while being effective to prevent spills and splashes.

The present invention overcomes the deficiencies in the prior art, by providing an emetic container that is easily accessed during times of nausea and prevents unwanted spills. This is accomplished by providing a container for receiving and containing emetic or like matter that is compact, easily transportable, and disposable.

SUMMARY OF THE INVENTION

In accordance with the present invention, a new and improved container for receiving and containing emetic or like matter is provided.

It is an objective of this invention to provide a container for receiving emesis that is compact and easily transportable.

It is a further objective of this invention to provide a container for receiving emesis that is disposable.

It is still a further objective of this invention to provide a container for receiving emesis device that is of durable and reliable construction.

It is still a further objective of this invention to provide a container for receiving emesis that has all of the advantages of the containers and none of the disadvantages.

To accomplish these objectives, the present invention provides for a container for receiving and containing emesis or other matter. The container includes a hollow body member that is open only at a first end and closed at a second end. The body member is disposed generally symmetrically about a central axis to define an interior space. There are receiving means carried on the first end of the body member adapted to facilitate receiving and directing emesis or other matter into the interior space. The container further includes restricting means carried on the body member adapted for restricting reverse flow of emesis or other matter. The body member is preferably formed of flexible material to allow the container to have a collapsed configuration wherein the first and second ends are closely spaced along the central axis and an expanded configuration wherein the first and second ends are widely spaced along the central axis.

According to one aspect of the invention, the restricting means comprises a local annular restriction located between the neck end and the base end, the restriction being operative to provide a gradual reduction in a cross-sectional area of the interior space above a minimum cross-sectional location and a gradual increase in the cross-sectional area below the minimum cross-sectional location, the annular restriction defining a lower wall adapted for restricting reverse flow of emesis or other matter within the interior space.

According to another aspect of the invention, the receiving means comprises an annular flange encompassing the neck end, the flange defining an opening in flow communication with the interior space, the flange being formed of flexible material adapted to facilitate receiving and directing emesis or other matter into the interior space.

According to another aspect of the invention, the annular flange includes reinforcing means at an outside edge thereof.

According toe another aspect of the invention the reinforcing means includes an additional amount of the flexible material rolled under at the edge.

According to another aspect of the invention, the base end includes a planar supporting base.

According to another aspect of the invention, the container further includes volume increasing means carried on the body member, the volume increasing means defining a pocket adapted for flow communication with the interior lower space.

According to another aspect of the invention the body member material is a member of the group consisting of elastomeric materials, and is preferably latex-free.

According to another aspect of the invention, the body member includes an upper sphere-like portion, a lower sphere-like portion, and a concave region extending between the upper and lower portions, wherein the concave region is operative to form the restricting means.

According to another aspect of the invention, a system is provided for receiving and containing associated emesis or other matter. The system includes a container including:

- a hollow body member having an open neck end and closed base end, the body member being disposed generally symmetrically about a central axis extending between the neck and base ends, the body member having an interior wall defining an interior space;
- receiving means carried on the body member at the neck end being adapted to facilitate receiving and directing emesis or other matter into the interior space;
- restricting means carried on the body member being adapted for restricting reverse flow of emesis or other matter within the interior space; and,
- wherein the body member is formed of flexible material, the body member being adapted to have a collapsed configuration wherein the neck end and the base end are closely spaced along the central axis and an expanded configuration wherein the neck end and the base end are widely spaced along the axis;

and a holder adapted to receive and support the container, the holder including:

a main body member having an opening adapted to receive the container therein;

means for closing the container at the neck of the body member;

means for storing plurality of containers, wherein the containers are in the collapsed configuration;

means adapted for cleaning emesis or other matter that is not received within the interior space.

According to another aspect of the invention, the systems further comprises containers adapted to be in a half fold configuration.

According to another aspect of the invention, the system further includes means for disposing of the containers after use.

According to another aspect of the invention, a holder adapted to receive and support a container for receiving and containing associated emesis or other matter is provided. The holder includes a main body member having an opening adapted to receive the container therein, the main body including gripping means surrounding the opening for gripping the container; a plurality of supporting legs depending from the main body member; and, a handle being operatively attached to the main body member.

According to another aspect of the invention, a combination of a container adapted for receiving and containing associated emesis or other matter and a holder adapted to hold and support the container is provided. The combination includes a container, the container having:

a hollow body member having an open neck end and closed base end, the body member being disposed generally symmetrically about a central axis extending between the neck and base ends, the body member having an interior wall defining an interior space;

receiving means carried on the body member at the neck end being adapted to facilitate receiving and directing emesis or other matter into the interior space;

restricting means carried on the body member being adapted for restricting reverse flow of emesis or other matter within the interior space; and, wherein the body member is formed of flexible material, the body member being adapted to have a collapsed configuration wherein the neck end and the base end are closely spaced along the central axis and an expanded configuration wherein the neck end and the base end are widely spaced along the axis; and, a holder adapted to receive and support the container, the holder including:

a main body member having an opening adapted to receive the container therein, the main body including gripping means surrounding the opening for gripping the container;

a plurality of supporting legs depending from the main body member; and, a handle being operatively attached to the main body member.

Other benefits and advantages of the invention will become apparent to those skilled in the art to which it pertains upon a reading and understanding of the following detailed specification.

BRIEF DESCRIPTION OF THE DRAWINGS

The invention may take physical form in certain parts and arrangement of parts, a preferred embodiment of which will be described in detail in this specification and illustrated in the accompanying drawings which form a part hereof and wherein.

DESCRIPTION OF THE PREFERRED EMBODIMENT

Figure 1:
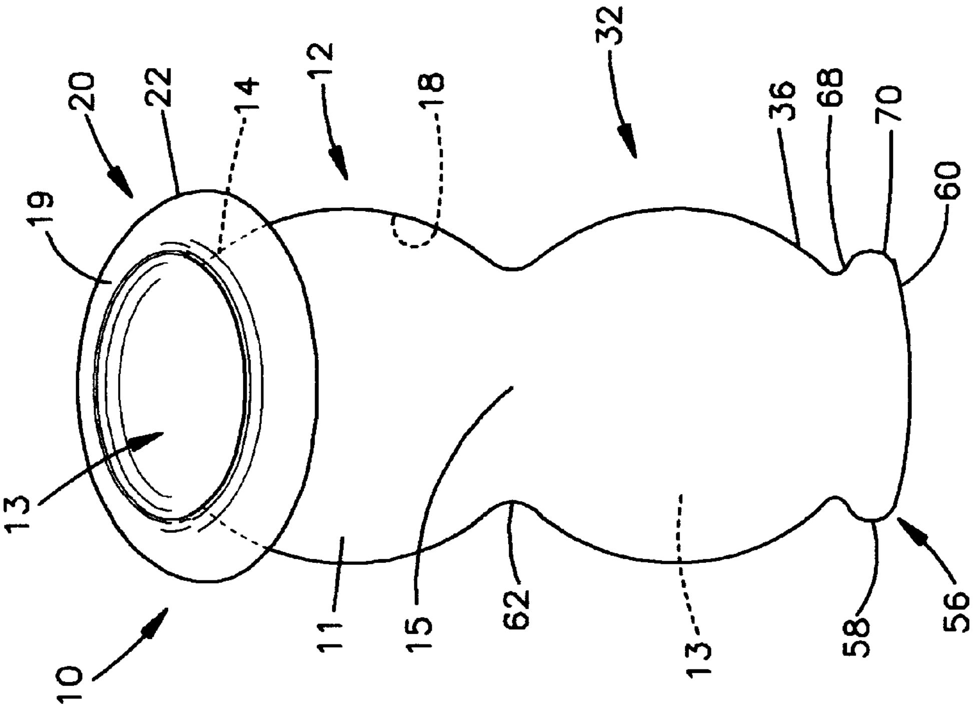
FIG. 1 is a perspective view of a container according to the invention.

Referring now to the drawings wherein the showings are for purposes of illustrating a preferred embodiment of the invention only and not for purposes of limiting the same, FIG. 1 shows one preferred embodiment of a container 10 according to the present invention. The container 10 is preferably formed of a unitary body member 11 defining an interior space 13. Although other configurations are contemplated, in the preferred embodiment, body member 11 has an hour-glass type shape with an upper body portion 12 and a lower body portion 32 being connected through a concave region 15. In the preferred embodiment, upper body portion 12 is open at its neck end 14. Upper body portion 12 is in fluid flow communication with lower body portion 32 through concave region 15. Lower body portion 32 is closed at its base end 36. Therefore emetic fluid entering the container 10 through the neck end 14 passes through concave region 15 and into lower body portion 32, where it is contained. The hour-glass shape of body member 11 facilitates the entry of emetic fluid into lower body portion 32, while hindering reverse flow through concave region 15 due to a splash-guard effect of the interior surface 18.

The upper and lower body portions 12, 32 have a preferably spherical-like shape. However the upper and lower body portions 12, 32 can have any shape chosen within sound engineering judgment.

The neck end 14 of the upper body portion 12 includes an annular flange 19, which forms a mouthpiece 20. The mouthpiece 20 communicates with the upper body portion 14 to transfer emetic material therein. In the preferred embodiment, the mouthpiece 20 is supported at its edge 22 to facilitate positioning mouthpiece 20 adjacent to the mouth of the user for receiving emesis therefrom. In the preferred embodiment, mouthpiece 20 is formed of flexible material and edge 22 includes excess material rolled under to provide support. In the preferred embodiment, the mouthpiece 20 is unitary with the body member 11. However, the mouthpiece 20 can be a separate component secured to the neck end 14.

Figure 2:
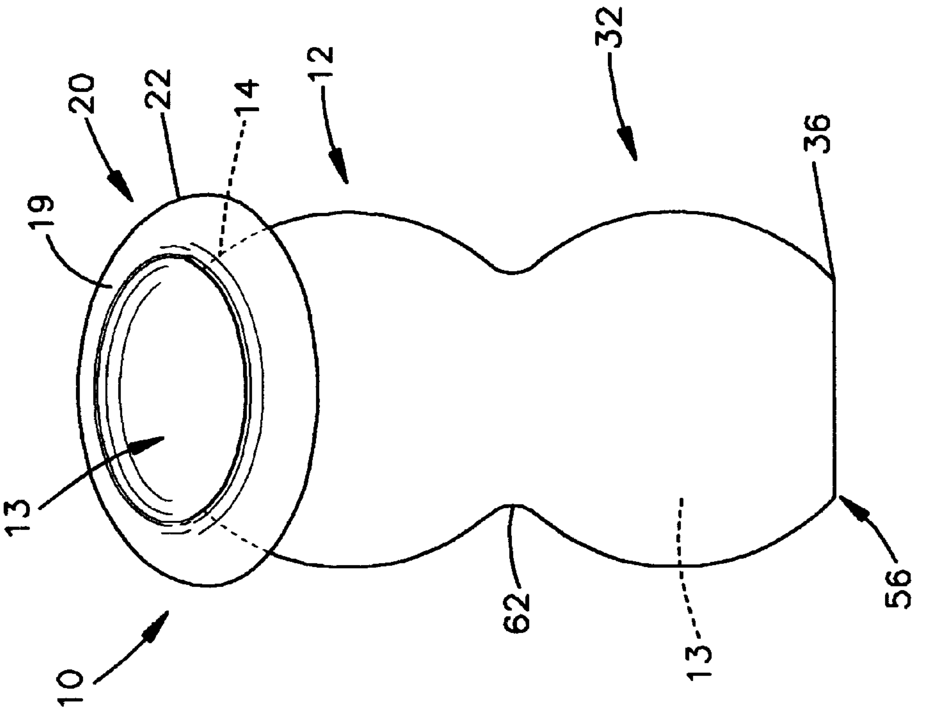
FIG. 2 is a perspective view of an alternate embodiment of a container according to the invention.

Turning to FIG. 1, in one preferred embodiment, the base end 36 may be open rather than closed. The base end in this embodiment is supported by base 56. The embodiment shown in FIG. 1 shows base 56 comprising side panel 58 having first and second ends 68,70 and a planar circular bottom 60. However, the base 56 can have any form that adequately supports the container 10. An alternate embodiment of base 56 is shown in FIG. 2, where the base end 36 is closed as previously described. In FIG. 2, base 56 is substantially planar and may integrally connect with the base end 36.

In the preferred embodiment, the container 10 is comprised of elastomeric material. Most preferably, the material is non-allergenic. In the preferred embodiment, the material used is latex-free. The material is preferably opaque, soft, flexible, lightweight and acid tolerant. However, the container 10 can be comprised of any material chosen within sound engineering judgment. Further, to increase the aesthetic appeal of the container 10, especially for children, the container 10 can be colored and/or insignias, such as cartoon characters, sport team logos, musicians, etc., can be placed thereon.

Figure 3:
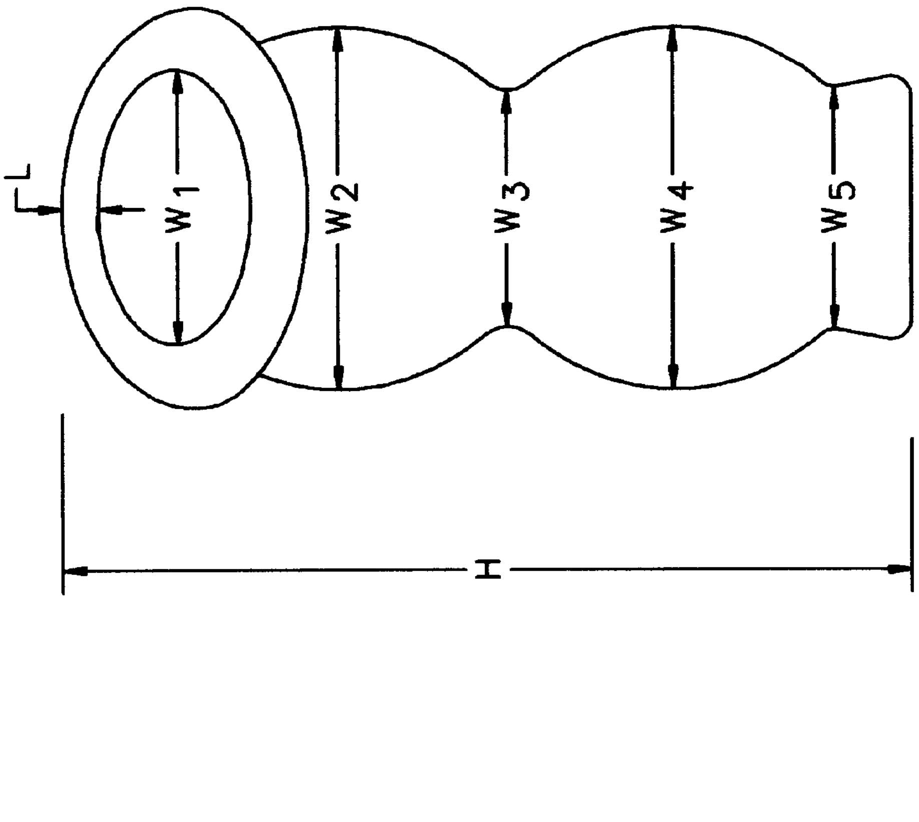
FIG. 3 is a perspective view of the container shown in FIG. 1.

With reference to FIG. 3, in the preferred embodiment, the container 10 has the following dimensions: a container 10 height, H, ranging from approximately 10½ inches to approximately 11½ inches, and more preferably about 11 inches, and most preferably approximately 10¾ inches; a maximum width, W2, W4, of the first and second body portions 12, 32 ranging from approximately 4½ inches to approximately 5½ inches, and most preferably approximately 5 inches; a width, W5, ranging from approximately 2 inches to approximately 3 inches, and most preferably approximately 2½ inches for the second end of the second body portion 36; a width, W1 to stretch and pull over the user's mouth, ranging from approximately 3 inches to approximately 4 inches, and most preferably approximately 3½ inches for the neck end 14 of the first body portion 12; a width, W3, ranging from approximately 3 inches to approximately 4 inches, and most preferably approximately 3½ inches at the location of splash back guard 62; and, a width, L, ranging from approximately ½ inch to approximately 1½ inches, and more preferably approximately 1 inch, and most preferably 1½ inches for the mouthpiece 20. However, these dimension illustrate only one preferred embodiment of the container 10 and are not given by way of limiting the invention. The container can 10 have any dimensions chosen within sound engineering judgment. For example, the dimensions could be reduced to create a container 10 specifically designed for children.

Figure 4:
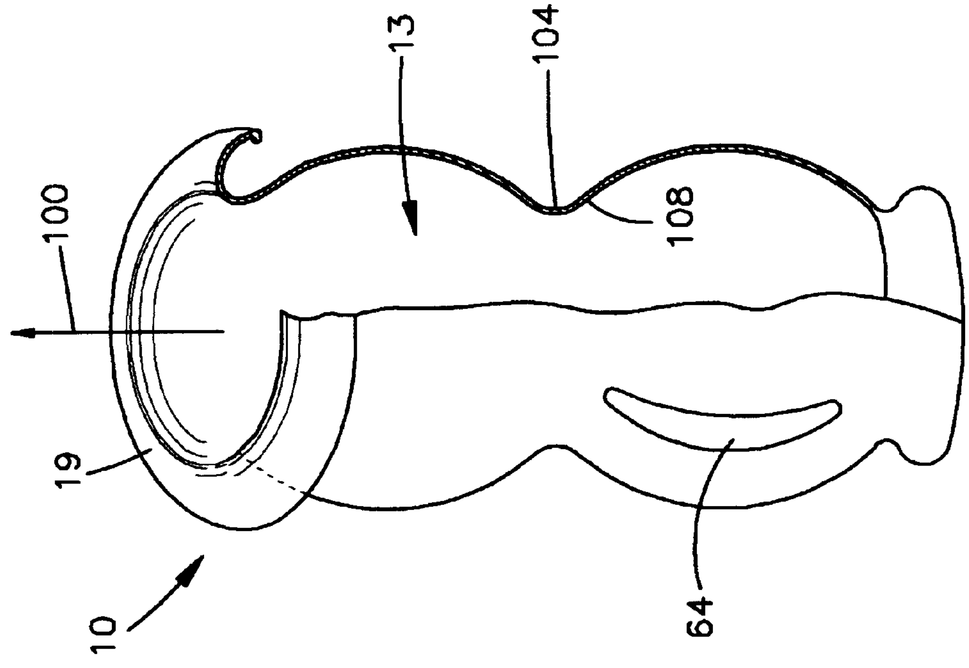
FIG. 4 is a partial cross-sectional view of yet another embodiment of a container according to the invention.

Yet another embodiment of the invention is illustrated in FIG. 4. The container 10 may optionally include expandable side pockets 64 that are in flow communication with the interior space 13. The expandable side pockets 64 may be located on either the upper or lower body portions 12,32, or both, and allow the body member 11 to increase in volume when the container 10 is filled with emesis or other matter.

Figure 6:
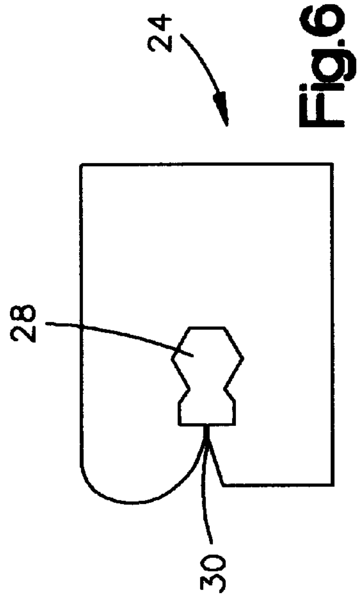
FIG. 6 is a top view of a tab.
Figure 5:
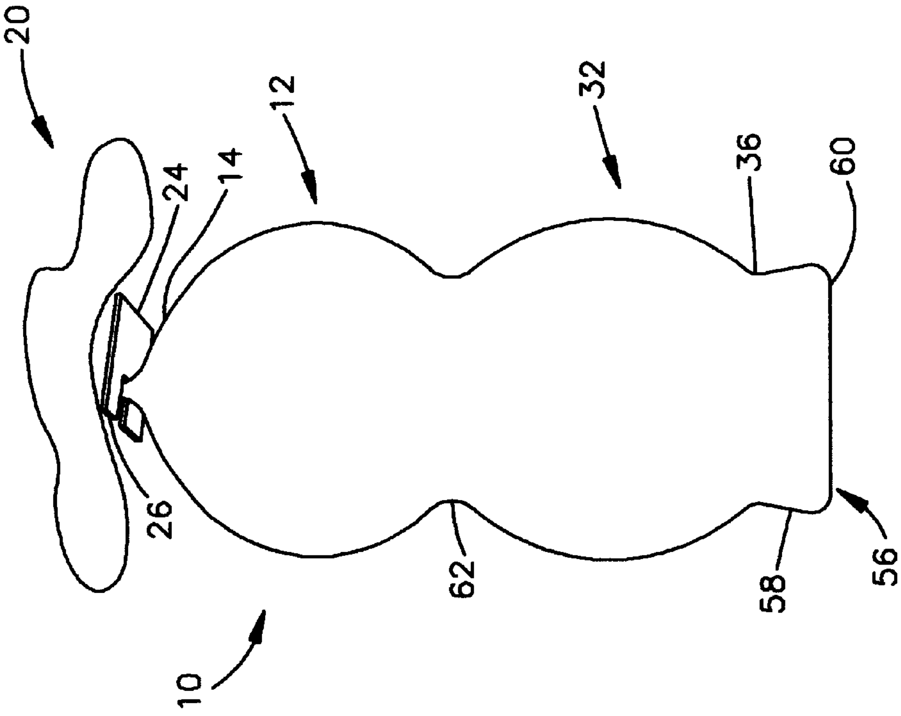
FIG. 5 is a perspective view of a container wherein a tab is utilized to close one end.
Figure 9:
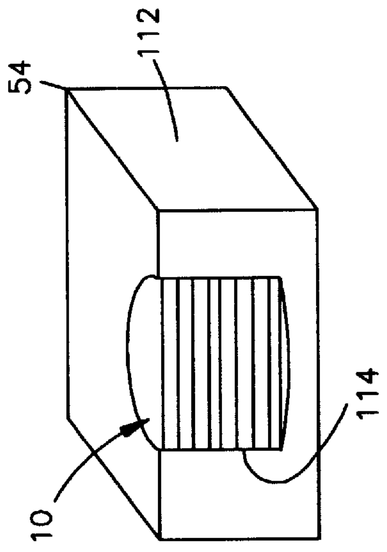
FIG. 9 is a perspective view of a storage/dispensing device for storing and dispensing a plurality of containers according to the invention; and, FIG. 10 is a front view of a wiping cloth for use in a system for receiving and containing emesis or other matter according to the invention.

FIGS. 5 and 6 illustrate a closing means 24 that may be used to close the neck end 14 of the body member 11. Preferably, the closing means 24 is a tab 26 having a substantially rectangular, planar shape. The tab 26 has an aperture 28 in one end and a slit 30 extending therein. The neck end 14 of the body member 11 is received by the first aperture 28 in the tab 26 and, thereby closes the body member 11. However, any closing means such as a twist tie, rubber band, or a clip may be used.

Figure 7:
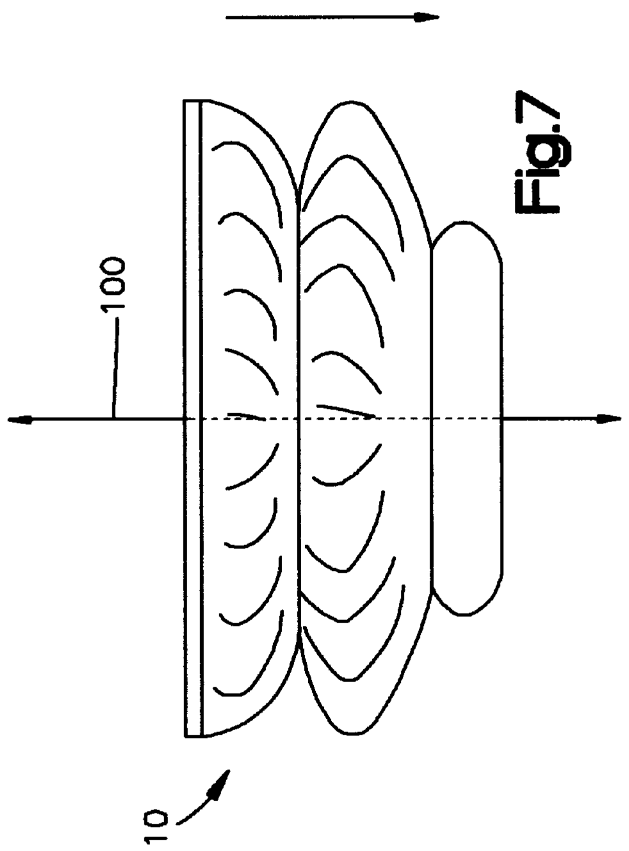
FIG. 7 is a side view of a container in a collapsed configuration.
Figure 11:
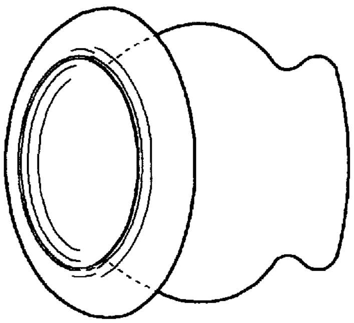
FIG. 11 is a perspective view of the present invention in the half-fold configuration.

The body member 11 is essentially a hollow tube-like structure being disposed generally symmetrically about a central axis 100 extending between the neck end 14 and the base end 36. In the preferred embodiment, the body member 11 is formed of flexible material whereby the container 10 has a stored configuration, which may be a half-fold configuration, as shown in FIG. 11, or a collapsible configuration. In the collapsible configuration, the container 10 is collapsible along the central axis 100 as shown in FIG. 7. In its collapsed configuration, the neck end 14 of the body member 11 is closely spaced to the base end 36. This compact configuration enhances an ability to readily store an unused container 10 as will be discussed later in this specification. This compact configuration provides advantages over devices known in the prior art. Although paper bags are foldable, the interior is not accessible until the bag is unfolded. However, even in its collapsed configuration, the interior space 13 of the container 10 of the present invention is accessible through the mouthpiece 20. The container 10 readily assumes its extended configuration when the mouthpiece 20 is lifted.

With reference to FIG. 4, the local annular restriction 104 is illustrated. The interior space 13 is associated with a cross-sectional area. Moving in a direction parallel to the central axis 100 from the neck end 14 to the base end 36, the restriction 104 provides a gradual reduction in the cross-sectional area until a minimum cross-sectional area is attained, then the cross-sectional area gradually increases. This construction creates a lower wall 108 that forms the splashguard 62.

In the preferred embodiment, the upper body portion 14 is generally spherically shaped, and the lower body portion 32 is also generally spherically shaped with the concave region 15 extending between the upper body portion 14 and the lower body portion 32. As shown in FIG. 4, in this preferred embodiment, the concave region 15 is operative to form the local annular restriction 104.

Figure 8:
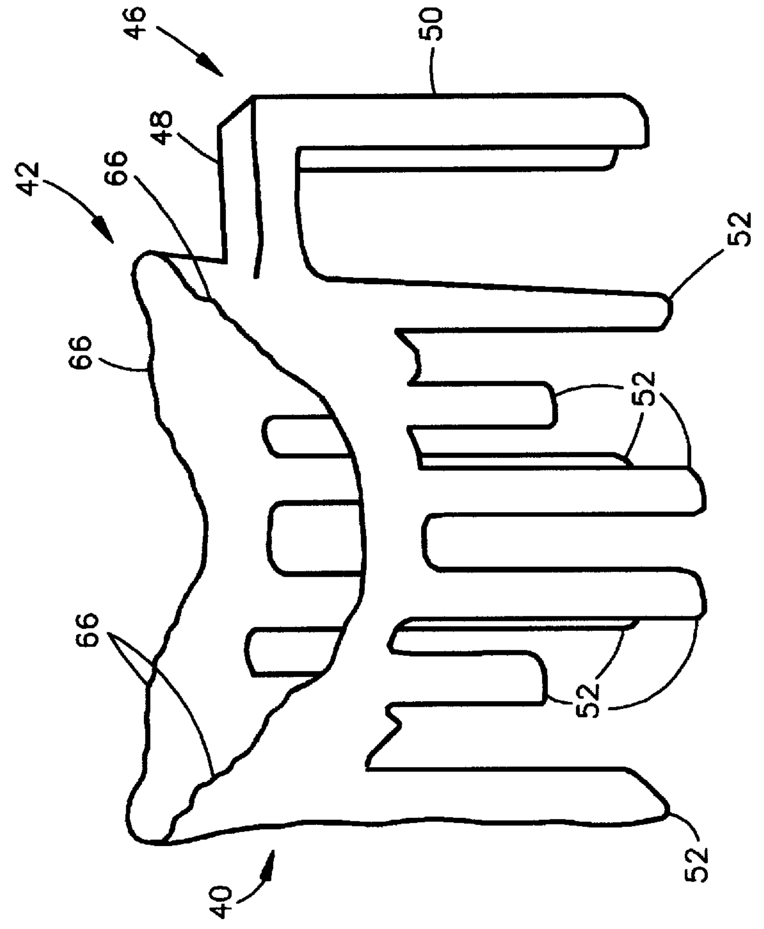
FIG. 8 is a perspective view of a holder for holding a container according to the invention.

In another preferred embodiment of the invention, there is provided a holder 40, shown in FIG. 8, for holding and supporting the container 10. The holder 40. The holder 40 includes a main body member 42 having an opening 44 therein adapted to receive a container 10. A plurality of leg members 52 depends from the main body member 42. In the preferred embodiment, at least four of the leg members 52 are adapted to support the holder 40 in an upright position. Additional leg members may be utilized, as in the illustrated embodiment, to stabilize the holder 40. In the preferred embodiment, a handle 46 is carried on the main body member 42.

In the preferred embodiment, the holder 40 has eight leg members 52. The handle 46 is a substantially L-shaped member having first and second ends 48, 50 with the first end 48 attached to the main body member 42 and the second end 50 for use in being received by the hand of a user. The second end 50 may also be utilized as a hanger so that the holder 40 can be positioned for easy access. For illustrative purposes only, and not by way of limiting the invention, in the preferred embodiment, the leg members 52 have a length of approximately 3 inches and a width of approximately ½ inch, the main body member 42 has a width of approximately 4½ inches, the first end of the handle 48 has a length of approximately 1 inch and the second end of the handle 50 has a length of approximately 2½ inches.

In the preferred embodiment, the holder 40 is formed of a disposable heavy press cardboard material. However, the holder 40 can be comprised of any material that adequately supports the container 10, such as plastic.

In the preferred embodiment, the holder 40 includes gripping means 66, such as teeth, surrounding the opening 44. The gripping means 66 are operable to engage the body member 11 at the neck end 14. In the preferred embodiment, the mouthpiece 20 can be extended over the opening 44 and the body member 11 is inserted through opening 44. Generally, any geometrical dimensions of the holder 40 may be chosen with sound engineering judgment to accommodate different uses and applications.

Figure 10:
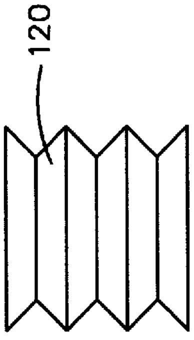

With reference to FIG. 8, the container 10 can be packaged in a tissue box styled storage/dispensing device 54. A plurality of containers 10 can be readily stored in a small space in their collapsed configuration. The storage/dispensing device 54 has a housing 112 adapted to accommodate the collapsed containers 10. A perforated region, not shown, is readily removable to create an opening 114 through which the containers 10 can be accessed. In the preferred embodiment, separate wiping cloths 120 are provided for the convenience of the user for cleaning up any spills of the emetic matter as shown in FIG. 10.

In an alternate embodiment of the invention, the flexible body member 11 is folded along a line perpendicular to the central axis 100 before placing in the storage/dispensing device 54.

The invention has been described with reference to a preferred embodiment. Obviously, modifications and alterations will occur to others upon a reading and understanding of this specification. It is intended to include all such modifications and alternations in so far as they come within the scope of the appended claims or the equivalence thereof.

Having thus described the invention, it is now claimed:

1. A container adapted for receiving and containing associated emesis or other matter comprising:

a hollow body member having an upper sphere-like portion with an open neck end and a lower sphere-like portion with a closed base end, said body member being disposed generally symmetrically about a central axis extending between said neck and base ends, said body member having an interior wall defining an interior space;

receiving means defined by said body member at said neck end being adapted to facilitate receiving and directing emesis or other matter into said interior space; and, restricting means defined by said body member being adapted for restricting reverse flow of emesis or other matter within said interior space;

wherein said body member is formed of flexible material, said body member being adapted to have a collapsed configuration wherein said neck end and said base end are closely spaced along said central axis and an expanded configuration wherein said neck end and said base end are widely spaced along said central axis.

2. The container of claim 1 wherein said restricting means comprises:

a local annular restriction located between said neck end and said base end, said restriction being operative to provide a gradual reduction in a cross-sectional area of said interior space above a minimum cross-sectional location and a gradual increase in said cross-sectional area below said minimum cross-sectional location, said annular restriction defining a lower wall adapted for restricting reverse flow of emesis or other matter within said interior space.

3. The container of claim 1 wherein said receiving means comprises:

an annular flange encompassing said neck end, said flange defining an opening in flow communication with said interior space, said flange being formed of flexible material adapted to facilitate receiving and directing emesis or other matter into said interior space.

4. The container of claim 3 wherein said annular flange includes reinforcing means at an outside edge thereof.

5. The container of claim 4 wherein said reinforcing means includes an additional amount of said flexible material rolled under at said outside edge.

6. The container of claim 1 wherein said base end includes supporting means.

7. The container of claim 6 wherein said supporting means includes a planar base.

8. The container of claim 1 further comprising:

volume increasing means defined by said body member, said volume increasing means defining a pocket adapted for flow communication with said interior space.

9. The container of claim 1 wherein said material is a member of the group consisting of elastomeric materials.

10. The container of claim 9 wherein said material is a latex-free material.

11. The container of claim 1 wherein said body member includes a concave region extending between said upper and lower portions, wherein said concave region is operative to form said restricting means.

12. A container adapted for receiving and containing associated emesis or other matter comprising:

a hollow body member having an upper sphere-like portion being open at a neck end and a lower sphere-like portion with a closed base end, said body member being disposed generally symmetrically about a central axis extending between said neck and said base ends, said body member having an interior wall defining an interior space;

an annular flange defined by said body member and encompassing said neck end, said flange defining an opening in flow communication with said interior space, said flange being formed of flexible material adapted to facilitate receiving and directing emesis or other matter into said interior space; and, a local annular restriction located between said neck end and said base end, said restriction being operative to provide a gradual reduction in a cross-sectional area of said interior space above a minimum cross-sectional location and a gradual increase in said cross-sectional area below said minimum cross-sectional location, said annular restriction defining a lower wall adapted for restricting reverse flow or emesis or other matter within said interior space;

wherein said body member is formed of flexible material, said body member being adapted to have a collapsed configuration wherein said neck end and said base end are closely spaced along said central axis and an expanded configuration wherein said neck end and said base end are widely spaced along said central axis.

13. A system adapted for receiving and containing associated emesis or other matter comprising:

a container, said container including:

a hollow body member having an upper sphere-like portion with an open neck end and a lower sphere-like portion with a closed base end, said body member being disposed generally symmetrically about a central axis extending between said neck and base ends, said body member having an interior wall defining an interior space;

receiving means defined by said body member at said neck end being adapted to facilitate receiving and directing emesis or other matter into said interior space;

restricting means defined by said body member being adapted for restricting reverse flow of emesis or other matter within said interior space; and, wherein said body member is formed of flexible material, said body member being adapted to have a collapsed configuration wherein said neck end and said base end are closely spaced along said central axis and an expanded configuration wherein said neck end and said base end are widely spaced along said axis; and, a holder adapted to receive and support said container, said holder including:

a main body member having an opening adapted to receive said container therein.

14. The system of claim 13 further comprising:

means for closing said container at said neck of said body member.

15. The system of claim 13 further comprising:

means for storing plurality of containers, wherein said containers are in said collapsed configuration.

16. The system of claim 13 further comprising:

means adapted for cleaning emesis or other matter that is not received within said interior space.

17. The system of claim 13 further comprising:

means for disposing of said containers after use.

18. A system adapted for receiving and containing associated emesis or other matter comprising:

a container, said container including:

a hollow body member having an upper sphere-like portion with an open neck end and a lower sphere-like portion with a closed base end, said body member being disposed generally symmetrically about a central axis extending between said neck and base ends, said body member having an interior wall defining an interior space;

receiving means defined by said body member at said neck end being adapted to facilitate receiving and directing emesis or other matter into said interior space;

restricting means defined by said body member being adapted for restricting reverse flow of emesis or other matter within said interior space; and, wherein said body member is formed of flexible material, said body member being adapted to have a stored configuration wherein said neck end and said base end are closely spaced along said central axis and an expanded configuration wherein said neck end and said base end are widely spaced along said axis;

a holder adapted to receive and support said container, said holder including:

a main body member having an opening adapted to receive said container therein;

means for closing said container at said neck of said body member;

means for storing and dispensing a plurality of containers, wherein said containers are in said stored configuration;

means adapted for cleaning emesis or other matter that is not received within said interior space; and, means for disposing of said containers after use.

19. The system of claim 18, wherein said stored configuration of said containers is a collapsed configuration.

20. The system of claim 18, wherein said stored configuration of said containers is a half-fold configuration.

21. In combination, a container adapted for receiving and containing associated emesis or other matter and a holder adapted to hold and support said container comprising:

a container, said container including:

a hollow body member having an upper sphere-like portion with an open neck end and a lower sphere-like portion with a closed base end, said body member being disposed generally symmetrically about a central axis extending between said neck and base ends, said body member having an interior wall defining an interior space;

receiving means defined by said body member at said neck end being adapted to facilitate receiving and directing emesis or other matter into said interior space;

restricting means defined by said body member being adapted for restricting reverse flow of emesis or other matter within said interior space; and, wherein said body member is formed of flexible material, said body member being adapted to have a collapsed configuration wherein said neck end and said base end are closely spaced along said central axis and an expanded configuration wherein said neck end and said base end are widely spaced along said axis; and, a holder adapted to receive and support said container, said holder including:

a main body member having an opening adapted to receive said container therein, said main body member including gripping means surrounding said opening for gripping said container;

a plurality of supporting legs depending from said main body member; and, a handle being operatively attached to said main body member.

* * * * *